(12) United States Patent
Wittig et al.

(10) Patent No.: US 6,348,338 B1
(45) Date of Patent: Feb. 19, 2002

(54) METHOD TO SEPARATE CELLS THAT HAVE BEEN MODIFIED WITH SUPERPARAMAGNETIC PARTICLES BY BALLISTIC TRANSFER

(76) Inventors: Burghardt Wittig, 4715 Town Center Dr., FFC 10856, Colorado Springs, CO (US) 80916-4709; Matthias Schroff, Bunzlauer Str 7, D-30853 Langenhagen (DE)

( * ) Notice: Subject to any disclaimer, the term of this patent is extended or adjusted under 35 U.S.C. 154(b) by 0 days.

(21) Appl. No.: 08/435,388

(22) Filed: May 5, 1995

(30) Foreign Application Priority Data

May 9, 1994 (DE) .......................................... 44 167 84

(51) Int. Cl.⁷ ............................................... C12N 15/00
(52) U.S. Cl. ................................ 435/172.1; 435/172.3; 935/53
(58) Field of Search ........................... 435/172.1, 172.3; 935/53

(56) References Cited

U.S. PATENT DOCUMENTS 4,945,050 A * 7/1990 Sanford et al. ........... 435/172.1
5,066,587 A * 11/1991 Jones et al. ............... 435/172.1
5,466,587 A * 11/1995 Fitpatrick-McElligott et al. ...... 435/172.1

OTHER PUBLICATIONS

Whitesides et al. (1983) Trends Biotechnol., 1(5), "Magnetic Separations in Biotechnology", pp. 144–148.*
Padmanabhan et al. (1988) Anal. Biochem., 170(2), "Purification of Transiently Transfected Cells by Magnetic Affinity Cell Sorting", pp. 341–348.*
Hebell et al. (1989) J. Immunol. Meth., 123(2), "The Isolation of Lymphocyte–B from Human Peripheral–Blood Using Antibodies Coupled to Paramagnetic Particles and Rosetting Techniques", pp. 283–291.*

* cited by examiner

*Primary Examiner*—Jon P. Weber

(57) ABSTRACT

The ballistic transfer transfection technology employs a cold gas shock wave to accelerate microprojectiles that carry matter into cells by mechanical force. The present invention relates to a method that enables separation of transfected cells by co-adsorbing polynucleic acids and nanometer-sized superparamagnetic particles onto the microprojectiles. The transfected cells are rendered magnetically susceptible and can thus be separated by retaining them in a strong magnetic field. The use of the technology in a clinical context is facilitated.

12 Claims, 1 Drawing Sheet

Fig. 1
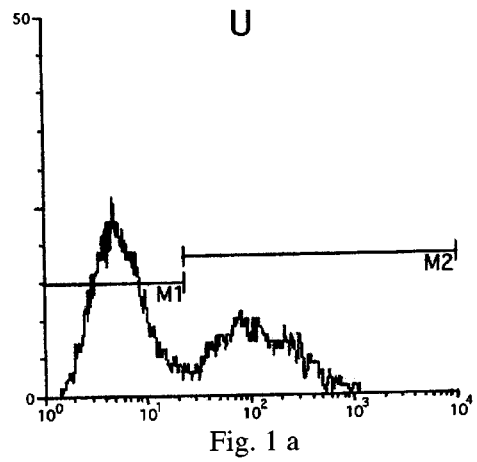
Fig. 1 a
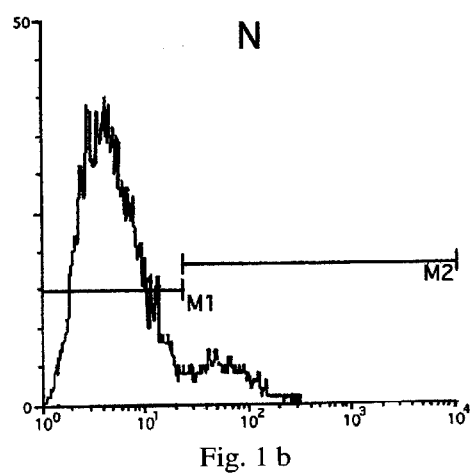
Fig. 1 b
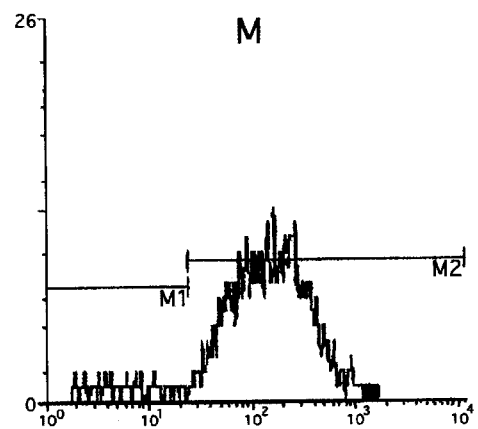
Fig. 1 c

METHOD TO SEPARATE CELLS THAT HAVE BEEN MODIFIED WITH SUPERPARAMAGNETIC PARTICLES BY BALLISTIC TRANSFER

FIELD OF THE INVENTION

This invention relates to a method whereby living cells modified by a biological substance, introduced into them by ballistic transfer, are efficiently separated from remaining unmodified cells.

BACKGROUND OF THE INVENTION

Many methods of modern cell biology require the transfer of matter, mainly nucleic acids, into living cells (hereafter referred to as transfection). Traditionally, this transfer of matter has been important to both the fields of biological and medical research. Recent progress, however, in the understanding of the body's functions as regarded to molecular mechanisms has led to the idea of treating human desease by using molecular approaches (colloquially referred to as "gene therapy"). Many of the biological methods suggested in this approach require the transfection of somatic cells. A number of techniques have been developed to achieve this aim: microinjection; electroporation; transfection by viral vectors or liposomes; and direct bombardment of cells with particles ("gene gun"). For a review on methods see *Methods in Enzymology* 217, (1993), pp. 461–655, (Academic Press, San Diego, Calif.).

Apart from microinjection, in which a single cell is injected directly with the transfecting matter, these methods suffer from a rather low and unreliable efficiency, efficiency being measured as percentage of successfully transfected cells out of total of treated cells. Microinjection's efficiency is very high; however, the number of treated cells is generally too low for this technique to be clinically valuable.

If the object of the transfection is to insert genetic information into the cell, then successful transfection requires the passage of the transfecting nucleic acid not only into the cell cytoplasm, but into the nucleus. The nuclear membrane is a barrier more difficult to cross than the cytoplasmic membrane. Many of the cells transfected by means of electroporation or lipofection that have incorporated the transfecting matter into their cytoplasm, will not express any genetic message transferred into them. For expression of any genetic message to happen, the genetic message has to pass into the nucleus. The transfection of cells with DNA by electroporation is most likely successful only when it happens during cell division, because the division process momentarily renders the nucleus permeable for the transfecting DNA.

In contrast, the ballistic transfection method achieves transport into the nucleus by the kinetic energy of the passing particle. The probability of nuclear passage of the microcarrier particle is governed by the ratio of nucleus diameter to cell diameter, which for many cells, is very favourable for nuclear passage. Thus, it can be expected that any clinical approach to transfection of cells with DNA would increase efficiency, employing the ballistic transfection method.

A current estimate of the number of transfected cells needed in a clinical protocol is in the order of $10^7$–$10^8$ cells. For the reasons given above, we believe that of the transfection methods mentioned, the ballistic transfer, i.e. directly bombarding cells with particles that carry the transfecting matter into the cells, has the greatest potential to achieve this aim.

Various embodiments of the idea of bombarding cells in order to achieve transfection have been published. They differ in the propulsion of the particles, the nature of the particles and various other aspects. A number of patents have been filed describing these embodiments (see: Jones, Frey, Gleason, Chee, Slightom: Gas driven microprojectile accelerator and method of use U.S. Pat. No. 5,066,587; Jones, Frey, Gleason, Chee, Slightom: Gas driven microprojectile accelerator WO 9111526, U.S. Pat. No. 471,216; Sanford, Wolf, Allen: Apparatus for delivering substances into cells and tissues in a non-lethal manner EP 0 331 855; Tome: improved particle gun EP 0 397 413; Brill, McCabe, Yang: Particle-mediated transformation of animal somatic cells WO 91/00359; Mets: Aerosol beam injector WO 91/00915; WO 91/02071; Johnston, Williams, Sanford, McElligott: Particle-mediated transformation of animal tissue cells WO 91/07487; Bruner, deVit, Johnston, Sanford: Improved method and apparatus for introducing biological substances into living cells WO 91/18991; Bellhouse, Sarphie: Ballistic apparatus. WO 9204439, GB 9018892.1). However, only one embodiment to our knowledge, is commercially manufactured. This embodiment is the "Biolistic" apparatus invented by John C Sanford and manufactured under licence from Cornell University and DuPont by Bio-Rad (Hercules, Calif.). The propulsion of the microcarriers is achieved by adsorbing the microcarriers to a macrocarrier polymer sheet, which is accelerated towards the cells by a cold gas shock wave. After retaining the macrocarrier, the microcarrier sheaf continues towards the target cell layer, eventually impacting and unloading the adsorbed transfecting matter into the cells.

The method of ballistic transfection implies that only a (sometimes large) fraction of the target cells is transfected successfully. The microcarrier sheaf is rarely homogeneous, and has to be of sufficiently small density in order not to kill too many of the target cells, which invariably suffer from stress exerted on them by both the shock wave and the impacting microprojectiles. A balance must be found between a high survival rate and a high transfection rate, which leaves part of the target cells untransfected.

In many of the plausible clinical uses, a separation of transfected cells from untransfected cells is desirable, if not strictly required. Ex vivo transfection of tumor cells for cancer gene therapy is only one example. The current state of the art employs time-consuming separation protocols based on expression of markers. The genetic information for these markers is introduced into the cell with the transfecting DNA. This procedure requires cell culture of the transfected cells ex vivo for a prolonged period of time, raising the risk of both contamination and alteration of cell characteristics. A method enabling a quick, simple separation of transfected cells would clearly be of great value.

Magnetic separation techniques have been in use in biology for years. These methods primarily employ para-ferromagnetic beads, the size of which ranges in micrometers. Paramagnetic particles of such size retain some residual magnetic orientation after removal of an external magnetic field, leading to aggregation in solution. Recently, a new separation technique has been introduced (Miltenyi: Methods and materials for high gradient magnetic separation of biological materials WO 90/07380; DE 3720 844) that is based upon the coupling of biological material onto submicroscopic-size magnetic particles. These particles have the property of being "super-paramagnetic," meaning their magnetic core is smaller than the the size of a Weiss domain: the area of similar magnetic dipole orientation within a paraferromagnetic solid. In the absence of an external magnetic field, these particles do not retain any macroscopic magnetic orientation; thus do not attract each other, making them ideal for suspension in fluids. Their retainment requires a very strong "high gradient" magnetic field, since the magnetic force exerted on the particle is small due to its minimal size. A typical separation apparatus employs a mesh of iron wool embedded in polymer, through which the suspension is passed. In the presence of a strong magnetic field, the local field inside the wool mesh is strong enough to retain the particles. After removal of the external field, the particles can be washed out.

BRIEF DESCRIPTION OF THE DRAWINGS

The cytograms show the results of fluorescence measurements. The abscissa represents fluorescence in log scale, the ordinate cell number. U represents unsorted cells after ballistic transfer; M and N represent the magnetic and nonmagnetic fractions, respectively.

BRIEF SUMMARY OF THE INVENTION

The invention refers to a method by which cells that have been transfected by ballistic transfer methods ("gene gun") can be separated from untransfected cells. It employs co-adsorption of nanometer-sized "superparamagnetic" particles and the transfecting matter onto the microcarriers. The microcarriers are accelerated towards the cells. They hit the cells and unload the magnetic particles into the cells, along with the transfecting matter. The magnetic particles render the cells susceptible to magnetic field forces. After the ballistic transfer procedure, the cells are suspended in medium and passed through a separation column within a strong magnetic field. Transfected cells are retained by the incorporated magnetic particles, whereas non-transfected cells are washed through. After removal of the external field, separation yields of over 90% successfully transfected cells are achieved.

The claimed method allows the easy separation of cells that have been hit by one or more microcarriers. After such contact, the cells are presumably loaded with the transported matter. In our experiments, we used fluorescence-tagged oligodesoxynucleotides to transfect cells from human cell culture lines by a procedure that employed the "Biolistic"-transfer technology marketed by "Bio-Rad." We found that after transfection, more than 95% of the surviving cells separated by the invention described here were marked with fluorescence, and, therefore, successfully transfected. This fluorescence reading constitutes a substantial increase compared to the same experiment conducted without separation, typically yielding a fluorescence-positive cell count of 40%.

It is conceivable to use other microcarriers than the 1.6 micron gold particles employed in the examples set forth within this disclosure. The separation technique is not confined to the apparatus, particles, cells or propulsion means of the microcarriers used here. More specifically, it is conceivable to use paramagnetic particles as both microcarriers and magnetic means of achieving the separation.

The claimed separation method is especially useful in the field of cancer gene therapy: An important approach to treating tumor patients is the immunization of the patient against the tumor cells. This is achieved by excision of tumor tissue, and transfection of excised tumor cells with plasmids carrying expressable genes that encode proteins. The encoded proteins, when expressed by the tumor cell, direct the immune system response against the cell. Among the proteins suggested in this context are cytokines interleukin 2 and 7, major histocompatibility complex proteins, growth factors and others.

After transfection, cells are incubated under conditions suited to trigger expression of the transfected gene for 24 h to 48 h. The cells are then irradiated to render them incapable of cell division, and given back into the patient subcutaneously in most cases. Alternatively, intravenous transfusion may be used if haemodynamic or other mechanisms of distribution and/or homing are intended. The irradiated cells continue to express their genetic programm, part of which is the transfected gene for the immunostimulant protein. The body's immune system responds to the transfected cells by mounting an immune response against the transfected tumor cells. The immune system, thus taught how to recognize and fight the tumor cells, continues to attack not only the transfected tumor cells but also the untransfected cells of tumor tissue that had not been excised and possible metastases.

For this approach, it is important to treat the patient with successfully transfected cells only. The achievable immune response is strongly dependent on the concentration of the expressed gene product. Any significant contamination of untransfected cells not only reduces the concentration of the gene product, but will tend to overgrow transfected cells during the 24 h to 48 h incubation period. Thereby, the concentration of the gene product of the transfected gene becomes exponentially diluted and clearly reduces the desired immune response. The present invention is the only separation method to our knowledge that enables the neccessary separation yields for gene therapy.

In the case of melanoma, leukemia and few other tumor tissues it is possible to obtain primary cell cultures of tumor cells relatively easy. These primary cell cultures are transfected preferably by ballistic transfer, because the present separation method provides for easy separation of transfected cells.

However, the advantage of the combination of ballistic transfer and magnetic separation becomes even more obvious in the case of cancers as mamma carcinoma, colon carcinoma and rectum carcinoma. These cancers are among the epidemiologically most relevant malignant deseases. Their dependancy of growth on tissue environment makes it impossible to establish a reliable primary cell culture and transfect them subsequently. If a few cells adhere to the petri dish and start to proliferate, they bear little immunological resemblance to the original tumor cells. If the approach outlined above is to be used to induce an immune response of the patient against the tumor, solid tumor tissue has to be treated. Within the relatively intact microenvironment of a slice of excised tumor tissue, the cells on the surface of the slice are a population representative of the tumor, as seen by the body's immune system.

Our approach is to transfect slices of 500 $\mu$m thickness, which corresponds to about 10 layers of cells. We estimate that by "shooting" at both sides of a tumor slice, we reach 20% of the cells in the slice, of which 10% to 40% are succesfully transfected, resulting in a net efficiency of 2% to 8% of treated tumor slice. It is obvious that a separation of successfully transfected cells is of paramount importance to this approach to treating these epidemiologically, and thus economically, most important cancers.

DETAILED DESCRIPTION OF THE INVENTION

EXAMPLE 1

According to one preferred embodyment, 30 $\mu$l of a suspension of colloidal gold (1.6 $\mu$m diameter, 30 mg/ml, Bio-Rad, Hercules, Calif.) are transferred onto a macrocarrier polymer sheet (Bio-Rad). The gold is allowed to sediment, and the supernatant is removed. The gold is resuspended in a mixture of one part aqueous solution of DNA (fluorescein-endlabeled oligodesoxynucletides 50 µg/ml) and one part suspension of colloidal superparamagnetic particles (65 nm diameter, Miltenyi GmbH, Bergisch Gladbach, Germany, used as purchased). The suspension of superparamagnetic particles may be dialysed against PBS (phosphate buffered saline) in order to remove residual sodium azide added to the storage buffer. After sedimentation, the supernatant is removed and the residual gold is allowed to dry.

300 µl of polylysine solution is put into the center of a petri dish (3.5 cm diameter) and incubated for 30 min. The solution is removed and the dish washed with PBS medium. $1 \times 10^5$–$2 \times 10^5$ cells (erythroleukemia cell line K 562) in 300 µl of RPMI medium (10% fetal calf serum) are transferred onto the centre of the petri dish and left for 10 min. Consecutively, 2 ml of RPMI medium (10% fetal calf serum) are added and the cells left to incubate at a temperature of 37° C. for two hours (50% $CO_2$).

The ballistic transfer is conducted according to the operating protocol supplied by the manufacturer of the employed apparatus (Biolistic PDS 1000/He, Bio-Rad). The rupture disc ruptures at 1100 psi. The pressure of the lower vacuum chamber is 508 mm (20 inches) Hg.

The separation procedure is conducted on a MACS-separation column (Miltenyi GmbH) according to the operating protocol of the manufacturer. The entire process is conducted at a temperature of 4° C.:

The cells are resuspended after transfection in 1 ml ice cold PBS/BSA medium (5 mM EDTA) and washed onto the column while in a magnetic field. The column is washed with three volumes of PBS/BSA medium (5 mM EDTA) at a flow rate of 0.3 ml/min. The fluid is retained and labeled N (non-magnetic). The magnetic field is removed and the column is flushed with one volume PBS/BSA medium (5 mM EDTA) in reverse direction to whirl up the retained cells. The magnetic field is applied again and the fluid is drained. The column is washed with four to five volumina of PBS/BSA medium (5 mM EDTA) at a flow rate of 0.6 ml/min.

The magnetic field is removed and the retained cells are washed from the column by flushing with 1 ml of PBS/BSA medium (5 mM EDTA) in short pulses. The collected fraction is labeled M (magnetic). The collected fractions are subsequently assayed for their fluorescence in a flow cytometry scanner (FACS) (Becton Dickinson, Heidelberg, Germany).

The cytograms in the drawing section show the results of the measurements: U is a measurement of the unsorted cells after ballistic transfer. The abscissa represents fluorescence in log scale, the ordinate cell number. M and N are the corresponding measurements for the magnetic and nonmagnetic fractions, respectively. Tables 1–3 show the counts of fluorescence events: the sum count $\Sigma$; the count for strong fluorescence signals M2 which can be attributed to living transfected cells; and the count for low fluorescence signals M1, representing nontransfected cells and debris.

TABLE 1

| U | E | % |
|---|------|-------|
| $\Sigma$ | 5715 | 100 |
| M1 | 3483 | 60.94 |
| M2 | 2236 | 39.13 |

TABLE 2

| N | E | % |
|---|------|-------|
| $\Sigma$ | 7471 | 100 |
| M1 | 6524 | 87.32 |
| M2 | 951 | 12.73 |

TABLE 3

| M | E | % |
|---|------|-------|
| $\Sigma$ | 2792 | 100 |
| M1 | 262 | 9.38 |
| M2 | 2531 | 90.65 |

EXAMPLE 2

According to another preferred embodiment, primary cultures of melanoma cells from a patient's tumor are transfected as following:

Melanoma cells are cultured in 800 ml cell culture flasks. The medium is removed, and adherent cells are washed once with ice-cold PBS. 2.5 ml of trypsin-EDTA (0.5 g Trypsin/l; 0.2 g EDTA/l; 0.85 g NaCl/l) is added, and the cells are incubated at a temperature of 37° C. for 2–5 min. Cell lysis by trypsination is to be ice-cold PBS, and the cells are transfered into a 50 ml centrifuge tube (Falcon®, Beckton Dickinson, Heidelberg, Germany). The cell culture flask is rinsed with 5 ml of ice-cold PBS, and added to the centrifuge tube. The cells are centrifuged at 400×g for 7 min. The supernatant is removed, and the cells are resuspended in ice-cold RPMI-medium.

The cell are counted, cell density is adjusted to $5 \times 10^6$–$1 \times 10^7$ cells per 10 ml. $5 \times 10^6$ to $1 \times 10^7$ cells are distributed into each of various 10 cm petri dishes and incubated over night (18 h) under standard cell culture conditions (37° C., 5% $CO_2$, 90% humidity).

Approximately, $8 \times 10^6$ to $1 \times 10^7$ cells remain adherent in each petri dish. The medium is removed, the cells are washed with ice-cold PBS, and all supernatant fluid is removed carefully. This is very important, as any liquid covering the cells decreases the transfection efficiency of the following transfection dramatically. The cells are transfected by ballistic transfer according to the operating protocol of the manufacturer of the employed apparatus (Biolistic PDS 1000/He, Bio-Rad).

A significant modification to the employed apparatus is the introduction of a modified pressure distributor into the upper part of the apparatus, which allows to employ seven macroprojectile launching devices simultaneously, on a 10 cm petri dish. The additional macroprojectile launching devices make possible the simultaneous transfection of the large numbers of cells mentioned. For a detailed description of the pressure distributor, see our related filing (U.S. Ser. No. 08/615,770) "Pressure distributor and multi-macrocarrier assembly for ballistic transfer transfection apparatus". The procedure is possible with the unmodified apparatus, only smaller petri dishes and, consequently, lower cell numbers are to be used. However, the clinical application for which the present separation method was conceived made neccessary a transfection of a large number of cells, for which reason the modified pressure distributor was invented.

A suspension of colloidal gold (1.6 $\mu$m diameter, 30 $\mu$l, 60 mg/ml, Bio-Rad, Hercules, Calif.) is transferred onto each of seven macrocarrier polymer sheets (Bio-Rad). The gold is allowed to sediment, and the supernatant is removed. The gold is resuspended in a mixture of three parts aqueous solution of DNA (plasmid pCMV-IL7, 1 mg/ml, carrying the human interleukin 7 coding sequence under control of a strong promoter found in the genome of cytomegalovirus) and one part suspension of colloidal superparamagnetic particles (65 nm diameter, Miltenyi GmbH, Bergisch Gladbach, Germany, used as purchased). The suspension of superparamagnetic particles may be dialysed against PBS (phosphate buffered saline) in order to remove residual sodium azide added to the storage buffer. After sedimentation, the supernatant is removed and the residual gold is allowed to dry.

The seven macrocarriers are fit into the macrocarrier launching devices of the modified headpiece. Alternatively, only one macrocarrier is fit into the original apparatus provided by Bio-Rad, and the procedure is repeated several times. The repetion, however, would undoubtedly produce a large increase in the number of cells killed by stress. The ballistic transfer is carried out: the rupture disc ruptures at 1550 psi; the pressure of the lower vacuum chamber is 508 mm (20 inches) Hg.

The cells are covered with 3 ml of ice-cold PBS and incubated on ice for 5 min to detach them from the petri dish. The cells are gently washed off the dish with a pipette. The resulting suspension is passed through a cell strainer (70 $\mu$m, Costar GmbH, Bodenheim, Germany), and the magnetic separation is conducted as described above.

EXAMPLE 3

According to another preferred embodiment, solid tumor tissue from primary colon carcinoma, liver metastasis of colon carcinoma, or rectum carcinoma is transfected as following:

Tumor tissue as removed from the patient is cooled on ice. Necrotic and connective tissue is removed as much as possible. Pieces of approximately 1 cm$^2$ are cut from the tumor, rinsed in ice-cold PBS, glued to the specimen mounting block of a vibratome 1000 sectioning system (TPI, St. Louis, Mo.) with specimen adhesive (TPI). The tumor is cut at a blade angle of 20°, the section thickness is 500 $\mu$m. Vibration and cutting speed have to be determined for each tumor individually.

After sectioning, the slices are stored in ice-cold PBS and transfected as soon as possible:

A suspension of colloidal gold (1.6 $\mu$m diameter, 30 $\mu$l, 60 mg/ml, Bio-Rad, Hercules, Calif.) is transferred onto a macrocarrier polymer sheet (Bio-Rad). The gold is allowed to sediment, and the supernatant is removed. The gold is resuspended in a mixture of three parts aqueous solution of DNA (plasmid pCMV-IL7, 1 mg/ml, carrying the human interleukin 7 coding sequence under control of a strong promoter found in the genome of cytomegalovirus) and one part suspension of colloidal superparamagnetic particles (65 nm diameter, Miltenyi GmbH, Bergisch Gladbach, Germany, used as purchased). The suspension of superparamagnetic particles may be dialysed against PBS (phosphate buffered saline) in order to remove residual sodium azide added to the storage buffer. After sedimentation, the supernatant is removed and the residual gold is allowed to dry.

The ballistic transfer is conducted according to the operating protocol supplied by the manufacturer of the employed apparatus (Biolistic PDS 1000/He, Bio-Rad). The rupture disc ruptures at 1550 psi. The pressure of the lower vacuum chamber is 508 mm (20 inches) Hg.

After transfection, the slice is twice passed through a cell strainer (70 $\mu$m) with gentle pressure, to render single cells for the following separation step. The magnetic separation is conducted as described above.

The results of the transfection procedures have been as following:

| tumor 1 | primary colon carcinoma |
| tumor 2 | liver metastasy (colon carcinoma) |
| tumor 3 | liver metastasy (colon carcinoma) |
| tumor 4 | liver metastasy (rectum carcinoma) |

| tumor No | cell count after dissociation ("non-separated") | | cell count transfected cells ("magn. fraction") | | cell count untransfected cells ("non-magn. fraction") | | Recov in % |
|---|---|---|---|---|---|---|---|
| 1 | $1.1 \times 10^7$ | 100% | $3.6 \times 10^5$ | 3.3% | $7.5 \times 10^6$ | 68.2% | 72 |
| 2 | $2.2 \times 10^7$ | 100% | $6.9 \times 10^5$ | 3.1% | $1.3 \times 10^7$ | 59.1% | 62 |
| 3 | $4.1 \times 10^7$ | 100% | $6.2 \times 10^5$ | 1.5% | $1.9 \times 10^7$ | 46.3% | 48 |
| 4 | $2.0 \times 10^7$ | 100% | $7.3 \times 10^5$ | 3.7% | $1.4 \times 10^7$ | 70.0% | 74 |

| tumor No | cell count after dissociation ("non-separated") | | cell count transfected cells ("magn. fraction") | | cell count untransfected cells ("non-magn. fraction") | |
|---|---|---|---|---|---|---|
| | pg IL-7 · $10^{-5}$ cells · m$^{-1}$ | pg/ total cells | pg IL-7 · $10^{-5}$ cells · m$^{-1}$ | pg/ total cells | pg IL-7 · $10^{-5}$ cells · ml$^{-1}$ | pg/ total cells |
| 1 | 16 | $1.7 \times 10^8$ | 47 | $1.7 \times 10^7$ | 11.5 | $8.6 \times 10^7$ |
| 2 | 60 | $1.3 \times 10^9$ | 163 | $1.1 \times 10^8$ | 27 | $3.5 \times 10^8$ |
| 3 | 41 | $1.7 \times 10^9$ | 247 | $1.5 \times 10^8$ | 27 | $5.1 \times 10^8$ |
| 4 | 39 | $7.8 \times 10^8$ | 150 | $1.1 \times 10^8$ | 17.5 | $2.5 \times 10^8$ |

What is claimed is:

1. Method to separate cells, consisting of
   a) introducing superparamagnetic particles into the cells wherein the particles are very small in relation to the size of the cells, by
      1) adsorbing said superparamagnetic particles onto particles of high density that are small in relation to the size of the cells (microcarriers), and
      2) accelerating said microcarriers in the direction of the cells in such a way that said microcarriers enter or pass through the cells and unload said superparamagnetic particles and any other adsorbed matter into the cells, rendering the cells susceptible to magnetic fields by virtue of the incorporated superparamagnetic particles;
   b) passing the cells through a magnetic field strong enough to retain the cells susceptible to magnetic fields, whereas nonmagnetic cells can be removed by washing; and c) recovering the cells retained by the magnetic field by removing the magnetic field.

2. The method according to claim 1, where said superparamagnetic particles are adsorbed onto the microcarriers in combination with a polynucleic acid.

3. The method according to claim 1 or 2, where the microcarrier is made of gold.

4. The method according to claim 1, where the superparamagnetic particles have a median diameter of 30–100 nm and the applied magnetic field is a high gradient field.

5. The method according to claim 1, where the microcarriers are accelerated into the cells by means of a cold gas shock wave.

6. The method according to claim 5, wherein the gas is helium.

7. The method according to claim 1, where the cells are eukaryotic cells.

8. The method according to claim 1, where the cells are mammalian cells.

9. The method according to claim 1, where the cells are cells of the human immune system.

10. The method according to claim 1, where the cells are human tumor cells.

11. The method according to claim 1, 5, 8, 9, 10 or 6, where the superparamagnetic particles are co-adsorbed onto said microcarriers with polynucleic acids carrying one or more sequences that code for cytokines, immune system markers or cytokine receptors, and a promoter that enables the cell to express said sequences.

12. The method according to claim 1, 5, 8, 9, 10 or 6, where the superparamagnetic particles are co-adsorbed onto said microcarriers with polynucleic acids carrying one or more sequences that are antisense compliments to nucleic acid sequences coding for cell cycle regulative factors, signal transduction components or fragments thereof, or ribozyme oligonucleic acids.

* * * * *